United States Patent [19]

Campbell

[11] 3,938,038

[45] Feb. 10, 1976

[54] METHOD AND APPARATUS FOR PROVIDING PRIMARY COINCIDENCE CORRECTION DURING PARTICLE ANALYSIS

[75] Inventor: Stephen K. Campbell, Hialeah, Fla.

[73] Assignee: Coulter Electronics, Inc., Hialeah, Fla.

[22] Filed: July 1, 1974

[21] Appl. No.: 484,580

[52] U.S. Cl. ... 324/71 CP; 235/92 CP; 235/151.31; 328/112; 328/117; 328/160
[51] Int. Cl.² ............... H03K 21/30; G06M 11/00
[58] Field of Search. 324/71 CP; 235/92 PC, 92 PL, 235/151.31; 328/112, 117, 160

[56] References Cited
UNITED STATES PATENTS 3,737,633   6/1973   Collineau ...................... 235/92 PL
3,864,551   2/1975   Oefinger ........................ 324/71 CP

*Primary Examiner*—Stanley D. Miller, Jr.
*Attorney, Agent, or Firm*—Silverman & Cass, Ltd.

[57] ABSTRACT

A method and apparatus are disclosed wherein each particle pulse developed in response to passage of particles in a particulate system through a sensing zone is integrated to develop a first voltage whose amplitude varies in accordance with the number of pulses. The pulses are also integrated to develop a second voltage whose amplitude varies in accordance with the duration and, therefore, the size of all of the particle pulses. The first and second voltages are multiplied together to yield an error corrected voltage representing an error corrected particle pulse count, which is then converted to an error corrected particle pulse count.

21 Claims, 2 Drawing Figures

3,938,038

METHOD AND APPARATUS FOR PROVIDING PRIMARY COINCIDENCE CORRECTION DURING PARTICLE ANALYSIS

BACKGROUND OF THE INVENTION

This invention is directed to particle counting methods and apparatuses which provide a voltage correction to a voltage representing the count of particle pulses so that coincidence phenomena resulting in fewer particle pulses being counted in a predetermined time period does not induce an error in the particle pulse count ultimately obtained. The particle counting methods and apparatuses concerned employ particle sensing zones wherein the presence of one particle within the zone masks or hides the presence of another particle which also may be within the sensing zone. This invention particularly is directed to, but not limited to, the correct determination of non-electrical properties, such as size and count of microscopic particles by measuring electrical properties (Patent Office Class 324–71NE).

Now well known in the art of electronic particle counting and analyzing is apparatus marketed primarily under the trademark "Coulter Counter," and owned by the assignee of this application. Such apparatus and portions thereof are disclosed in several U.S. Pat. Nos.,: for example,: 2,656,508; 2,985,830; and 3,259,842 (Class 324–71). A significantly important portion of such Coulter type of apparatus is the minute scanning aperture or scanning ambit or sensing zone relative to or through which pass and are detected and counted, single particles at a rate often well in excess of one thousand per second. Because of the physical parameters of the scanning aperture, and particle concentration, coincidence of two particles in the scanning ambit occurs quite often.

It has been found that once a particle pulse produced by the presence of a particle in the scanning ambit exceeds the threshold setting of the apparatus and is detected, no other pulse will be produced in response to other particles in the scanning ambit until such times as the first particle has cleared the sensing zone. As the presence of a first particle masks a second particle causing a coincidence error the coincidence error is a function of the time that detected particles are in the scanning ambit, and the total coincidence error is a function of the total time that particles are in the scanning aperture during the detecting and counting process. Since the coincidence error is a function of the time that each particle is in the scanning aperture, it can also be said that the coincidence error is a function of the duration of each particle pulse produced and detected in response to passage of a particle through the scanning ambit. It has also been found that the coincidence error is functionally related to the rate at which particles pass through the scanning ambit, and therefore, the particle pulse repetition rate.

SUMMARY OF THE INVENTION

In practicing the invention, a method is provided for automatically correcting a particle pulse count subject to coincidence error. The method includes the steps of:
a. developing a first signal which varies in accordance with the number of particle pulses;
b. developing a second signal which varies in accordance with the duration of the particle pulses;
c. combining the first and second signals to develop an error corrected signal representing the error corrected particle pulses count.

An apparatus for automatically correcting a particle pulse count subject to coincidence error includes an accumulation device which is operative in response to the particle pulses to develop a first signal that varies in accordance with the number of particle pulses. An error correction device is operative in response to the duration of the particle pulses to develop a second signal which varies in accordance with the duration of the particle pulses. A combining device coupled to the accumulation device and the error correction device is operative to combine the first and second signals to develop an error corrected signal representing the error corrected particle pulse count. A converter circuit also can be employed and can be coupled to the combining device for converting the error corrected signal to an error corrected particle pulse count.

DETAILED DESCRIPTION OF THE INVENTION

Figure 1:
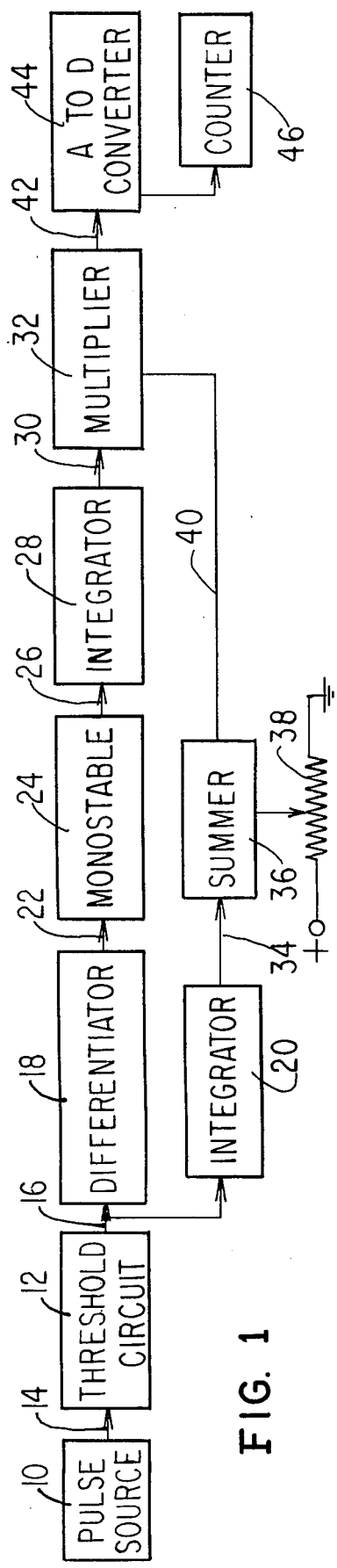
FIG. 1 is a block diagram of an apparatus embodying the features of this invention.

Referring to FIG. 1, a pulse source 10 couples particle derived pulses to threshold circuit 12 via conductor 14. The pulse source 10 may, for example, be a Coulter type of particle detector such as is shown and described in U.S. Pat. Nos. 2,656,508 and 3,259,842 wherein particle pulses are developed in response to the passage of particles in a particulate system through a sensing zone of the aperture tube. Each pulse developed by pulse source 10 has an amplitude which is a function of the size of the particle causing the particle pulse. It is now well known in the art that the pulse width or duration of each particle pulse is also a function of the size of the particle causing the particular particle pulse.

Threshold circuit 12 is operative in response to particle pulses coupled thereto, in excess of a predetermined amplitude to develop pulses of fixed amplitude at conductor 16. The duration of the pulses developed at conductor 16 would be equal to the period for which the particle pulses coupled to threshold circuit 12 exceed the predetermined amplitude. The fixed amplitude pulses developed by threshold circuit 12 at conductor 16 are coupled to a differentiator circuit 18 and an integrator circuit 20.

Differentiator 18 is operative in response to each fixed amplitude pulse coupled thereto via conductor 16 to develop a voltage spike or pulse of very short duration which is coupled via conductor 22 to monostable multivibrator 24. Monostable multivibrator 24, commonly known as a one shot, will change states in response to each differentiator pulse coupled thereto and develop an output signal of fixed amplitude and fixed duration. It is to be understood, of course, that for purposes of this application the period of the output pulse developed by monostable multivibrator 24 is shorter than the period between differentiator pulses coupled from differentiator 18. This means that the period of monostable multivibrator 24 must be shorter than the highest repetition rate of pulses from pulse source 10.

The pulses of fixed amplitude and duration developed by monostable multivibrator 24 are coupled via conductor 26 to integrator 28. Integrator 28 will integrate the pulses coupled from monostable 24 and develop an integration voltage which is proportional to the total number of pulses coupled from monostable multivibrator 24 and, therefore, is proportional to the total number of pulses coupled from pulse source 10. The integration voltage developed by integrator 28 is coupled via conductor 30 to one input of an analog multiplier circuit 32.

As previously noted, the pulses developed by threshold circuit 12 are also coupled via conductor 16 to integrator circuit 20, and vary in duration in accordance with the duration of the particle pulses. Integrator circuit 20 will integrate each pulse coupled thereto and develop an integration voltage which is proportional to the duration of that pulse. The integration voltage of each pulse is summed with the integration voltage of all preceding pulses in order to develop an integration voltage which is proportional to the total duration of all of the particle pulses received. As the voltage is proportional to the total duration of all of the particle pulses received, and as the duration of each particle pulse and, therefore, the duration of all of the particle pulse is functionally related to the time the particles are in the sensing zone, the integration voltage developed by integrator 20 is functionally related to the total time that detected particles are in the sensing zone.

In the preferred embodiment, the voltage developed by integrator circuit 20 is a relatively small correction voltage, hereinafter termed the error correction voltage. This voltage is coupled via conductor 34 to a summer circuit 36. A second input to summer circuit 36 is derived from a reference source which may, for example, be a potentiometer 38 adjusted to provide a one-volt reference potential to summer circuit 36. The reference potential is summed with the integration voltage from integrator circuit 20 in summer circuit 36 in order to obtain a voltage which is greater than one volt, and coupled via conductor 40 to a second input of analog multiplier circuit 32.

In analog multiplier circuit 32, the integration voltage coupled from integrator 28 via conductor 30 and representing the total number of pulses received, is multiplied by the voltage coupled from summer circuit 36 via conductor 40 representing the total pulse duration. The product voltage developed by this multiplication process in analog multiplier circuit 32, is coupled via conductor 42 to an analog to digital (A/D) converter 44. A/D converter 44 will convert the analog voltage at conductor 42 to a digital equivalent which is coupled to counter 46. Counter 46 will develop a number representing the error corrected particle pulse count in response to the digital signal from analog to digital converter 44.

Figure 2:
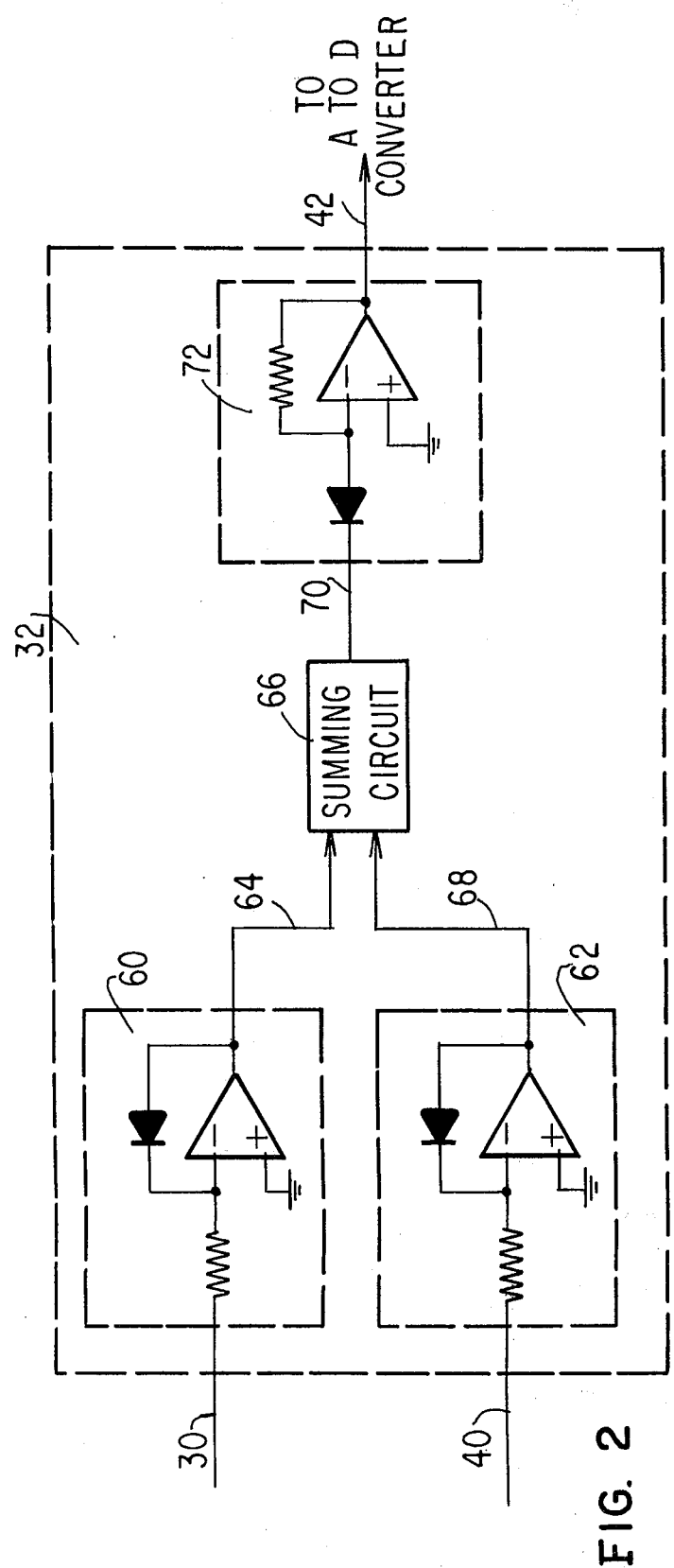
FIG. 2 is a combination schematic and block diagram of a multiplier circuit shown in FIG. 1.

Referring to FIG. 2, the multiplier circuit 32 of FIG. 1 is shown in greater detail. The integration voltage developed by integrator circuit 28 is coupled via conductor 30 to a logarithmic conversion circuit 60, and the error correction voltage developed at the output of summer circuit 36 is coupled via conductor 40 to a logarithmic conversion circuit 62. Logarithmic conversion circuits 60 and 62 are identical and are of the type now well known in the art which develop an output signal voltage which is proportional to the logarithm of the input voltage. The output voltage of logarithmic conversion circuit 60 is coupled via conductor 64 to one input of summing circuit 66 and the output of logarithmic conversion circuit 62 is coupled via conductor 68 to the second input of summing circuit 66.

Summing circuit 66 adds the voltages coupled thereto via conductors 64 and 68 and develops an output voltage equal to the sum of the two at conductor 70. Adding the logarithmic equivalent of two voltages is the same as multiplying the two voltages together and is the way such multiplication is performed via use of electronic circuitry. The voltage developed at conductor 70 is coupled to an antilog conversion circuit 72.

Antilog conversion circuit 72 develops an output voltage which is the antilog of the voltage at its input. As the voltage on conductor 70 at the input of antilog conversion circuit 72 is a logrithmic equivalent voltage, the output of antilog conversion circuit 72 developed at conductor 42 is equal to the voltage from which the logarithmic equivalent voltage is derived, which is equal to the product of the voltages developed at conductors 30 and 40.

It is to be understood that other modifications of the above noted apparatus are envisioned as being within the scope of this invention. For example, threshold circuit 12, can be a window type threshold circuit such as is shown and described in U.S. Pat. No. 3,259,842, which only develops output pulses if the pulses coupled from the pulse source 10 have an amplitude which falls within a predetermined range.

The method for correcting a particle pulse count subject to coincidence error is also envisioned as being within the scope of this invention. This method includes the steps of (a) developing a first voltage which varies in amplitude in accordance with the number of particle pulses; (b) developing a second voltage which varies in amplitude in accordance with the duration of the particle pulses; (c) multiplying the first and second voltages together to develop an error corrected voltage which represents the error corrected particle pulse count.

It is to be further understood that other modifications of the method and apparatus described are capable of being made without departing from the spirit or scope of the invention as defined in the appended claims.

What is desired to be secured by Letters Patent of the United States:

1. A method for automatically correcting a particle pulse count subject to coincidence error wherein particle pulses are developed in response to passage of particles in a particulate system through a sensing zone, including the steps of:
   developing a first signal which varies in accordance with the number of particle pulses,
   developing a second signal which varies in accordance with the duration of the particle pulses,
   combining said first and second signals to develop an error corrected signal representing the error corrected particle pulse count.

2. The method of claim 1 further including the step of converting said error corrected signal to an error corrected particle pulse count.

3. The method of claim 1 wherein said step of developing said first signal includes the steps of detecting particle pulses in excess of a first amplitude, and developing said first signal in response to said detected particle pulses.

4. The method of claim 1 wherein said step of developing said second signal includes the steps of detecting particle pulses in excess of a first amplitude, and integrating each of said portions of said particle pulses in excess of said first amplitude to develop said second signal.

5. The method of claim 1 wherein said step of combining said first and second signals includes the step of algebraically multiplying said first signal by said second signal to develop said error corrected signal.

6. The method of claim 5 further including the step of converting said error corrected signals to an error corrected particle pulse count.

7. The method of claim 1 wherein the step of developing said first signal includes the steps of detecting particle pulses in excess of a first amplitude, developing first pulses of fixed amplitude and duration in response to each detected particle pulse, and integrating each of said pulses to develop said first signal.

8. The method of claim 1 wherein said step of developing said first signal includes the steps of developing a first pulse of fixed amplitude and duration in response to each of said detected particle pulses, and integrating each of said first pulses to develop said first signals.

9. The method of claim 8 wherein said step of developing said second signal includes the steps of integrating said particle pulses to develop said second signal.

10. An apparatus for automatically correcting a particle pulse count subject to coincidence error wherein particle pulses are developed in response to passage of particles in a particulate system through a particle sensing device, said apparatus including in combination,
   accumulation means operative in response to said particle pulses to develop a first signal which varies in accordance with the number of particle pulses,
   error correction means operative in response to the duration of said particle pulses to develop a second signal which varies in accordance with the duration of said particle pulses,
   combining means coupled to said accumulation means and said error correction means and operative to combine said first and second signals to develop an error corrected signal representing the error corrected particle pulse count.

11. The apparatus of claim 10 further including converter means coupled to said combining means for converting said error corrected signal to an error corrected particle pulse count.

12. The apparatus of claim 10 wherein said first and second signals and said error corrected signal are voltages and further including analog to digital converter means coupled to said combining means for converting said error corrected voltage to an error corrected particle pulse count.

13. The apparatus of claim 10 wherein said combining means is a multiplier means for multiplying said first and second signals together and developing said error corrected signal.

14. The apparatus of claim 10 further including threshold means coupled to said accumulation means and said error correction means, said threshold means being operative to develop detection signals in response to particle pulses of a predetermined amplitude, said accumulation means being operative in response to said detection signals to develop said first signal, said error correction means being operative in response to said detection signals to develop said second signal.

15. The apparatus of claim 14 wherein said accumulation means includes monostable means, coupled to said threshold means and operative in response to each of said detection signals to develop a monostable signal, and integration means coupled to said monostable means and operative to integrate such monostable signals and develop said first signal.

16. The apparatus of claim 14 wherein said threshold means develops said detection signals for the period said particle pulses exceed said predetermined amplitude, said error correction means including second integration means operative to integrate said detection signals and develop said second signal which varies in accordance with the duration of said particle pulses.

17. The apparatus of claim 14 wherein said threshold means develops said detection signals for the period said particle pulses exceed said predetermined amplitude, said error correction means including second integration means operative to integrate said detection signals and develop a second integration signal which varies in accordance with the duration of said detection signals, summing means coupled to said second integration means and a source of reference, said summing means summing said second integration signal and a reference signal from said reference source to develop said second signal.

18. The apparatus of claim 10 wherein said accumulation means includes monostable means operative in response to each of said particle pulses to develop a monostable signal and integration means coupled to said monostable means and operative to integrate said monostable signal to develop said first signal.

19. The apparatus of claim 10 wherein said error correction means includes second integration means operative to develop a second integration signal which varies in accordance with the duration of the particle pulses, and summing means coupled to said second integration means and a reference source said summing means summing said second integration signal and a reference signal from said reference source to develop said second signal.

20. In a particle analyzer subject to coincidence error wherein particle pulses are developed in response to passage of particles in a particulate system through a sensing zone, the improvement comprising,
   accumulation means operative in response to said particle pulses to develop a first signal which varies in accordance with the number of particle pulses received,
   error corrections means operative in response to the particle pulses to develop a second signal which varies in accordance with the duration of particle pulses,
   combining means coupled to said accumulation means and said error correction means for combining said first and second signals to develop an error corrected signal representing the error corrected particle pulse count.

21. The apparatus of claim 20 further including converter means coupled to said combining means for converting said error corrected signal to an error corrected particle pulse count.

* * * * *